US012734305B2

(12) United States Patent
Bech et al.

(10) Patent No.: US 12,734,305 B2
(45) Date of Patent: Sep. 15, 2026

(54) DRUG DELIVERY DEVICE ASSEMBLY AND ACCESSORY FOR DRUG DELIVERY DEVICE

(71) Applicant: AMGEN INC., Thousand Oaks, CA (US)

(72) Inventors: Carsten Bech, Thousand Oaks, CA (US); Jakob Halkjaer Pedersen, Frederiksberg (DK); Joshua Jay Dudman, Copenhagen (DK); Adrianus Gerardus Verschuren, Frederiksberg (DK); Chiushun Dan, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 618 days.

(21) Appl. No.: 18/032,014

(22) PCT Filed: Nov. 1, 2021

(86) PCT No.: PCT/US2021/057512

§ 371 (c)(1),
(2) Date: Apr. 14, 2023

(87) PCT Pub. No.: WO2022/098593

PCT Pub. Date: May 12, 2022

(65) Prior Publication Data

US 2023/0277778 A1 Sep. 7, 2023

Related U.S. Application Data

(60) Provisional application No. 63/109,603, filed on Nov. 4, 2020.

(51) Int. Cl.
*A61M 5/315* (2006.01)
*A61M 5/20* (2006.01)
(Continued)

(52) U.S. Cl.
CPC .......... *A61M 5/31576* (2013.01); *A61M 5/20* (2013.01); *A61M 5/3129* (2013.01); *A61M 5/3287* (2013.01); *A61M 2205/583* (2013.01)

(58) Field of Classification Search
CPC .. A61M 5/31576; A61M 5/20; A61M 5/3129; A61M 5/3287; A61M 2205/583;
(Continued)

(56) References Cited

U.S. PATENT DOCUMENTS 4,208,588 A * 6/1980 Rudin .................... G21F 5/018 250/496.1
2003/0229308 A1 12/2003 Tsals et al.
2016/0296716 A1 10/2016 Cabiri et al.

FOREIGN PATENT DOCUMENTS

WO WO-2020/219672 A1 10/2020

OTHER PUBLICATIONS

International Search Report and Written Opinion for Application No. PCT/US2021/057512 dated Feb. 23, 2022.

* cited by examiner

*Primary Examiner* — Theodore J Stigell
(74) *Attorney, Agent, or Firm* — MARSHALL, GERSTEIN & BORUN LLP; Michael P. Furmanek

(57) ABSTRACT

A drug delivery device assembly is provided, including an injector housing, a needle assembly, a drive assembly, and a reflective surface. The injector housing may include a body with a proximal end, a distal end, a longitudinal axis extending between the proximal end and the distal end, and at least one window. The needle assembly is at least partially disposed within the body and may include a syringe barrel containing a medicament and a needle or a cannula, wherein at least a portion of the syringe barrel positioned such as to be visible through the at least one window. The drive assembly is at least partially disposed within the body and
(Continued)

operably coupled with the needle assembly to urge the medicament through the needle or cannula during an injection sequence. The reflective surface is positioned with respect to the window such as to increase visibility of the syringe barrel.

16 Claims, 6 Drawing Sheets

(51) Int. Cl.
*A61M 5/31* (2006.01)
*A61M 5/32* (2006.01)

(58) Field of Classification Search
CPC .............. A61M 2209/088; A61M 5/42; A61M 2005/2006; A61M 2005/3125; A61M 2209/084
See application file for complete search history.

DRUG DELIVERY DEVICE ASSEMBLY AND ACCESSORY FOR DRUG DELIVERY DEVICE

CROSS-REFERENCE TO RELATED APPLICATION

This is the United States national phase of International Patent Application No. PCT/US2021/057512, filed Nov. 1, 2021, which claims priority to U.S. Provisional Patent Application No. 63/109,603, filed Nov. 4, 2020, the entire contents of each of which are hereby expressly incorporated herein by reference.

FIELD OF THE INVENTION

This disclosure generally relates to a drug delivery device assembly and accessory for a drug delivery device. More particularly, the disclosure generally relates to an assembly and/or an accessory that includes a reflective surface positioned with respect to a drug delivery device window such as to increase visibility of a syringe barrel of the drug delivery device.

BACKGROUND

Drugs are administered to treat a variety of conditions and diseases. Autoinjectors (e.g., pen style autoinjectors) and on-body injectors offer several benefits in delivery of medicaments such as drugs and/or therapeutics. One of the benefits can include simplicity of use, as compared with traditional methods of delivery using, for example, conventional syringes. Autoinjectors may be used to deliver many different medicaments with varying viscosities and/or desired volumes.

It may be desirable for autoinjector users to inspect and/or observe certain characteristics of the autoinjector before and/or during use. Autoinjector instructions for use ("IFU") may instruct, encourage, or recommend such inspection actions. For example, a user may desire to or be instructed to inspect a medicament via an autoinjector viewing window before using an autoinjector, such as to check for particulates, discoloration, or contaminants. A user may desire to or be instructed to observe the viewing window during the injection process, or at least before removing the autoinjector from contact with the patient's skin. More specifically, during the injection sequence the user may observe the decreasing volume of the medicament and the advancement of plunger stopper urging the medicament from the drug delivery device to determine when the injection is complete. These steps may reduce the likelihood of premature removal of the device from the delivery site, which can result in an incomplete dosage being delivered due to the drug spraying onto the skin surface.

It may be desirable for autoinjector users to maintain a particular force level and/or orientation during the injection. Autoinjector and Accessory IFUs may instruct, encourage, or recommend such actions. For example, a user may desire to or be instructed to maintain a constant or baseline force and/or to maintain the autoinjector in an orientation perpendicular to the injection site during the injection sequence. These steps may increase the likelihood of a complete and successful injection and/or reduce pain or discomfort.

However, some autoinjector users may find it awkward, uncomfortable, or otherwise inconvenient to apply the desired force at the desired orientation while also observing the viewing window. For example, some users may prefer to aim their gaze in a direction generally parallel with and/or along a longitudinal axis of the autoinjector. Such an orientation may permit the user to generally ensure that the autoinjector remains perpendicular to the injection site. However, such an orientation may not be conducive to observing the viewing window, which is typically on the side of the autoinjector.

Another potential issue with existing autoinjector designs includes instability during injection, which may occur even if the user attempts to hold the device in the desired orientation as discussed above. As another example, an instability may be due to the interaction between the device and the patient's skin. Autoinjectors typically have a feature on the front of the device that acts to unlock or initiate the injection when pressed against a user's skin. The reliability of the activation can be dependent upon the condition of the skin or tissue where the drug is injected where less stable tissue may result in difficulty with activation. The activation requires a specific force to be applied to the device and that force is transferred to the user's skin. The force is translated into a pressure and, depending upon the surface area of the device that interfaces with the user's skin, this pressure must significantly displace the user's tissue until sufficient force has been achieved to unlock or initiate the injection. This can result in requiring additional forceful application of the autoinjector onto the injection site, which may cause significant discomfort and hesitation in administering the medicament in the patient.

As described in more detail below, the present disclosure sets forth a drug delivery device assembly and an accessory for drug delivery devices, such as autoinjectors, that embodies advantageous alternatives to existing systems and methods, and that may address one or more of the challenges or needs mentioned herein, as well as provide other benefits and advantages.

SUMMARY

A drug delivery device assembly is provided, including an injector housing, a needle assembly, a drive assembly, and a reflective surface. The injector housing may include a body with a proximal end, a distal end, a longitudinal axis extending between the proximal end and the distal end, and at least one window. The needle assembly is at least partially disposed within the body and may include a syringe barrel containing a medicament and a needle or a cannula, wherein at least a portion of the syringe barrel positioned such as to be visible through the at least one window. The drive assembly is at least partially disposed within the body and operably coupled with the needle assembly to urge the medicament through the needle or cannula during an injection sequence. The reflective surface is positioned with respect to the window such as to increase visibility of the syringe barrel.

The assembly may include a plunger stopper disposed within the syringe barrel and operably coupled with the drive assembly to urge the medicament through the needle or cannula during the injection sequence. The reflective surface may be positioned with respect to the window such as to increase visibility of the plunger stopper during the injection sequence. More specifically, the reflective surface may be positioned with respect to the window such that during the injection sequence the plunger stopper is visible via the reflective surface from a position along the longitudinal axis and proximal of the proximal end of the injector housing.

The assembly may include an adapter coupling the reflective surface and the injector housing. The adapter may include a sleeve portion configured to receive at least a portion of the injector housing. The adapter may include a base portion defining a distal portion of the adapter and the sleeve portion may extend from the base portion in a direction generally parallel to the longitudinal axis.

The reflective surface may generally define a reflector axis such that the reflector axis and the longitudinal axis define an angle between 15 and 75 degrees. The angle may be between 30 and 60 degrees; between 40 and 50 degrees, or approximately 45 degrees. The reflective surface may include a concave portion curved around the reflector axis and may be generally aligned with the window. The reflective surface may be a mirror and may be glass.

An accessory for a drug delivery device is also provided, including a base portion configured to be operably coupled with a drug delivery device having a window and a reflective surface extending from the base and positioned with respect to the window such as to increase the visibility of the syringe barrel.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description.

DETAILED DESCRIPTION

Generally speaking, pursuant to these various embodiments, a drug delivery device (e.g., an autoinjector or other injector) is coupled with or used in conjunction with an accessory to increase visibility of certain components or portions of the drug delivery device. For example, the accessory may include a reflective surface positioned with respect to a window of the drug delivery device such as to increase visibility of the syringe barrel.

The term "about" as used herein means +/−10% to the smallest significant digit. The term "patient's skin" may refer to the users uncovered, naked, or bare skin and/or the user's skin as it is covered by clothing, bandage, or other covering.

Figure 1:
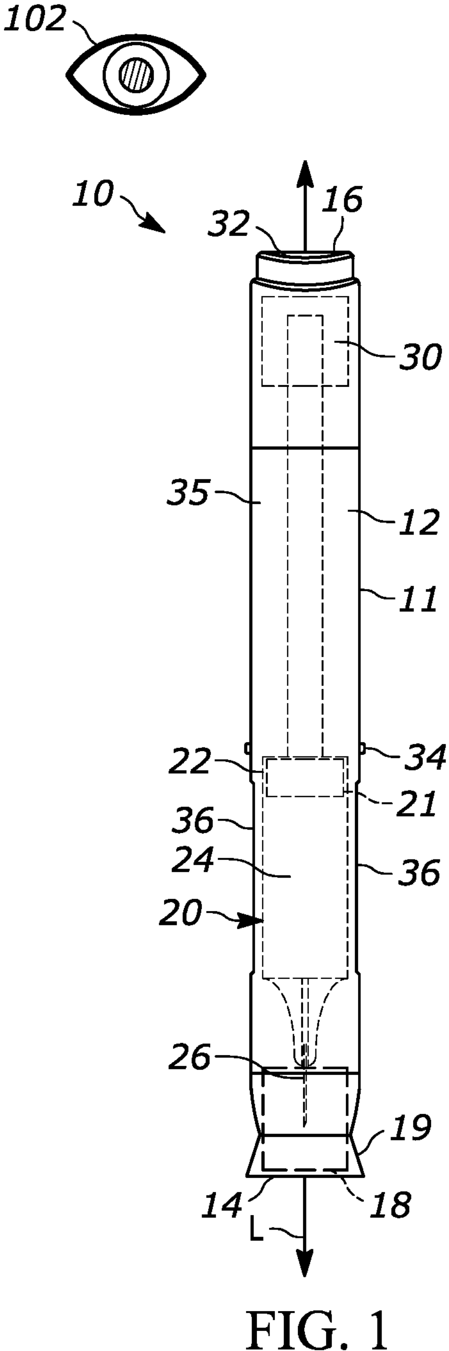
FIG. 1 is a perspective view of an exemplary drug delivery device that may be utilized with aspects of the present disclosure.

As illustrated in FIG. 1, an example injector 10 generally includes an injector housing 11 defining a housing 12 that includes a distal end 14, a proximal end 16, and a longitudinal axis L extending between the distal and proximal ends 14, 16. The injector 10 distal end 14 includes a generally cylindrical shaped needle shield 18 that assists with actuation of the injector 10 and a needle cap 19 that covers the needle shield 18 prior to use of the injector. A needle assembly 20 is at least partially disposed within the housing 12 at or near the distal end 14, and includes a syringe barrel 22 that contains a medicament 24, a plunger stopper 21 disposed within the syringe barrel 22, and a needle or a cannula 26 that is used to inject the medicament 24 into a patient. In the illustrated example, the needle or cannula 26 is initially positioned within the housing 12 prior to activation, and may protrude through an opening in the distal end 14 during drug delivery.

A drive assembly 30 is also at least partially disposed within the housing 12 and is operably coupled to the needle assembly 20. The drive assembly 30 may include an actuator button 32 positioned at or near the proximal end 16 of the housing 12 that initiates actuation of the drive assembly 30. In operation, a user removes the needle cap 19, places the needle shield 18 against the injection location (e.g., on their leg or their stomach), and actuates the actuator button 32. This actuation causes a drive mechanism (in the form of a spring, a motor, a hydraulic or pressurized mechanism, etc.) of the drive assembly 30 to exert a driving force on a portion of the needle assembly 20, such as the plunger stopper 21, that causes the needle or cannula 26 to be inserted through the opening of the housing 12 and into a patient and/or that further causes the medicament 24 to be urged from the syringe barrel 22, out the needle or cannula 26, and into the patient. In some versions, the patient may manually insert the needle or cannula 26, and actuation of the drive mechanism 30 only includes urging the plunger stopper 21 in the distal direction thereby causing the medicament 24 to be urged from the syringe barrel 22, out the needle or cannula 26, and to the patient. The injector 10 may not include an actuator button and may instead be activated by movement of the needle shield 18 alone, rather than an actuator button plus movement of the needle shield. The injector 10 may not include an actuator button and may instead be activated by movement of the needle shield 18 alone, rather than an actuator button plus movement of the needle shield.

The injector 10 may include any number of additional features and components that may assist and/or enhance the functionality of the device. In the illustrated example, one or more knobs 34 project from an outer surface 35 of the housing 12 as an anti-roll feature. The one or more knobs 34 may be integrally formed with the housing 12 of the injector 10 or may be coupled to the outer surface 35 by welding, adhesive, or by another adhering method. Additionally, a viewing window 36 positioned at or near the syringe barrel 22 provides a visual indication of the remaining quantity of drug during administration. The needle shield cap shields the needle 26 and prevents unintentional activation of the injector 10 and deployment of the needle or cannula 26. The needle shield 18 acts to unlock or initiate the injection when the needle shield 18 is pressed against a patient's skin. The activation of the drive assembly 30 requires a specific force to be applied to the needle shield 18 of the injector 10 and that force is transferred to the users skin. In other examples, the injector 10 may additionally include one or more electronic modules that are coupled to the housing 12, the needle assembly 20, the drive assembly 30, and/or any other components of the injector 10. Further, the injector 10 may also include any number of safety mechanisms such as a retraction mechanism, damping mechanism, and the like.

The present example of the drug delivery device 10 takes the form of an autoinjector or pen-type injector, and, as such, may be held in the hand of the user over the duration of drug delivery. The drug delivery device 10 may be suitable for self-administration by a patient or for administration by caregiver or a formally trained healthcare provider (e.g., a doctor or nurse). However, various implementations and configurations of the drug delivery device 10 are possible. In other examples, the drug delivery device 10 may be configured as a multiple-use reusable injector.

Figure 2:
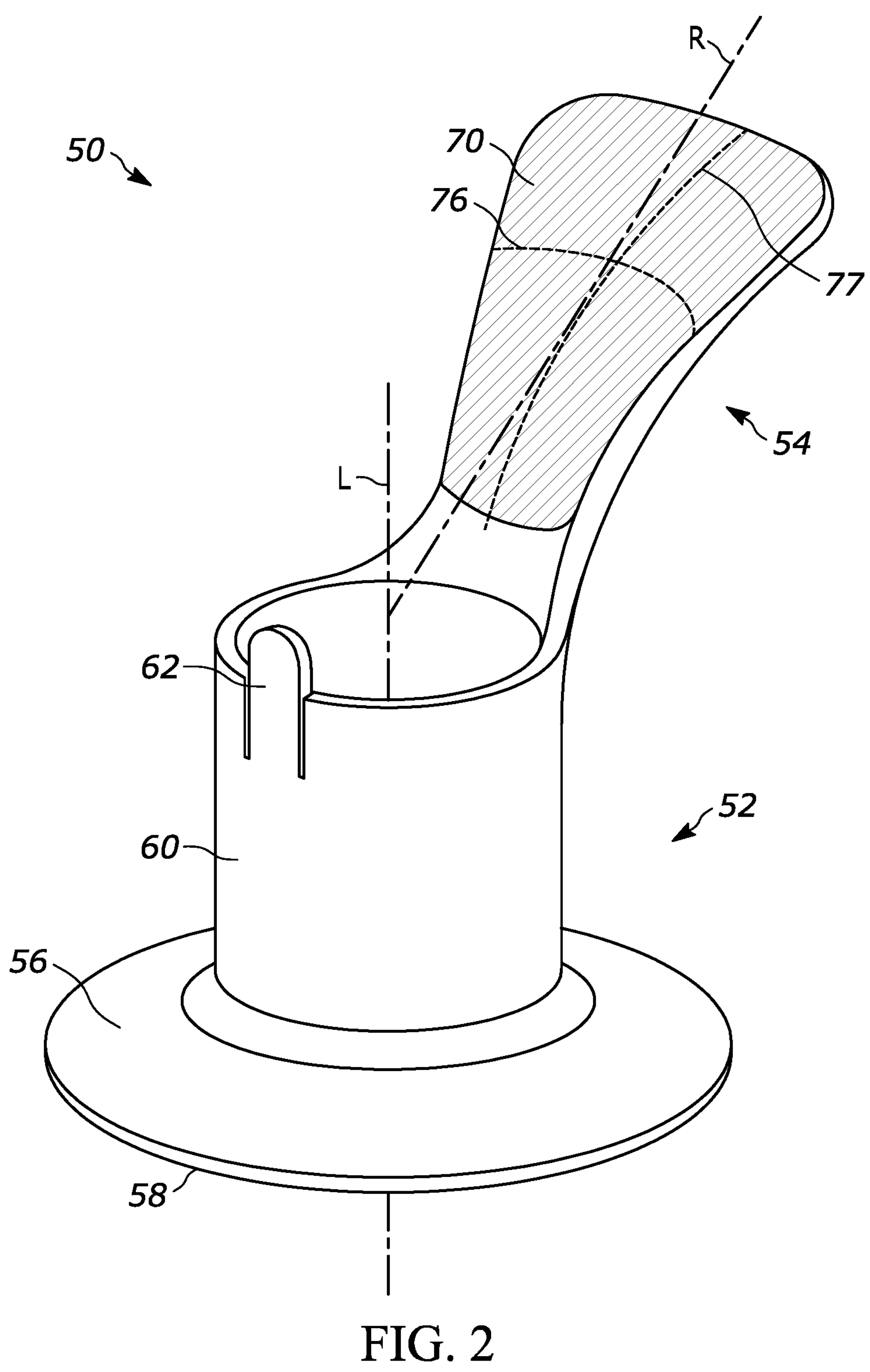
FIG. 2 is a perspective view of an exemplary accessory for a drug delivery device according to aspects of the present disclosure, having a reflective surface positioned such as to increase visibility of certain components or portions of the drug delivery device.

As illustrated in FIG. 2, an exemplary accessory 50 according to aspects of the present disclosure is shown. The accessory 50 may be utilized with an injector such as that shown in FIG. 1. The accessory 50 includes a reflective surface 70 positioned such as to increase visibility of certain components or portions of the drug delivery device. For example, the accessory 50 may increase the visibility of the plunger stopper 21 during the injection sequence. It may be desirable for a user to observe the viewing window 36 during the injection process, or at least before removing the injector 10 from contact with the patient's skin. More specifically, during the injection sequence the user may observe the decreasing volume of the medicament 24 and/or the plunger stopper 21 urging the medicament 24 from the injector 10 to determine when the injection is complete. Doing so may reduce the likelihood of premature removal of the device from the delivery site, which can result in an incomplete dosage being delivered due to the drug spraying onto the skin surface.

The exemplary accessory 50 shown in FIG. 2 includes an adapter 52 configured to be coupled with an injector and a flange 54 defining or supporting the reflective surface 70. The adapter 52 includes a base portion 56 defining a distal portion 58 of the adapter 52 and a sleeve portion 60 extending from the base portion 56, in a direction generally parallel to the longitudinal axis L of the injector 10 when the injector 10 is coupled with the accessory 50. The base portion 56 provides the user with a wider surface for contacting the user's skin, such that the contact forces acting on the user's skin may be more spread out, the users skin may be less likely to buckle or fold during contact, and/or it may be easier for the user to hold the drug delivery device in the desired orientation (perpendicular to the injection site). The accessory 50 may further include a latching component 62 that helps selectively couple the accessory 50 with the injector. For example, the latching component 62 shown in FIG. 2 is a flexible arm with a ridge 64 (FIG. 3) on the inner side thereof that is configured to abut the distal wall of the viewing window 36 and prevent movement between the accessory 50 and the injector unless and until the latching component 62 is moved away from the injector.

The accessory 50 may be a single, one-piece component that has at least one portion thereof that is reflective, namely the reflective surface 70. Alternatively, the reflective surface 70 may be a separate component, such as a mirror made of glass, polymer, or metal, that is coupled with the remaining portions of the accessory 50. For example, the reflective surface 70 may be overmolded with the flange 54 or may be coupled to the flange 54 via an adhesive or a fastener.

The flange 54 and/or the reflective surface 70 may generally define a reflector axis R (FIGS. 2 and 4), namely an axis defining the centerpoint of the flange 54. The reflector axis R and the longitudinal axis L define an angle 74 that may be between 15 and 75 degrees, 30 and 60 degrees, 40 and 50 degrees, or approximately 45 degrees. The angle 74 may be selected in view of several factors, as discussed below. Also, the angle 74 may be adjustable, as is also discussed below. The reflective surface 70 may be flat or it may have a contoured shape. The flange 54 and the reflective surface 70 shown in the Figures each have a contoured shape, namely a concave portion 76 curved around the reflector axis R. The contoured shape may help improve the visibility of the viewing window by focusing on the same. The flange 54 may also have a curvature in another direction, such as a convex portion 77. The convex portion 77 may have a contour shown in FIG. 2 and may also help improve the visibility of the viewing window by focusing on the same.

The position of the flange 54 may be fixed with respect to the adapter 52 or the flange 54 may be adjustable with respect to the adapter 52 so the user may adjust the position and/or the angle 74 of the reflective surface 70. For example, the flange may have a portion, such as the base portion, comprised of a flexible or deformable material. Additionally or alternatively, the flange may be coupled with the adapter via a ball joint, a hinge joint, or another adjustable fixture.

During operation, the accessory 50 may increase visibility of the plunger stopper 21 during the injection sequence in various ways, such as by increasing and/or modifying the areas from which a user is able to view the plunger stopper 21. For example, referring to FIG. 1, a user whose eyes are in a position 102, adjacent to the longitudinal axis L and proximal of the proximal end 16 of the injector 10, likely will not be able to observe the viewing window 36 without further assistance. Conversely, a user whose eyes are in the same position 102 with respect to an injector/accessory assembly 110 shown in FIG. 4 likely will be able to observe the viewing window 36 via the reflective surface 70, as discussed in more detail below. The position 102 shown in FIGS. 1 and 4 may be a desirable position for design of the angle of the reflector axis R because users may prefer to aim their gaze (e.g., to have a sightline) in a direction generally parallel with and/or along a longitudinal axis of the autoinjector. Such an orientation may also permit the user to keep their viewpoint angle parallel with the direction of force applied to the autoinjector. However, as discussed above, different users may have different preferred sightlines. To this end, it may be desirable for the flange to be movable with respect to the adapter, as discussed above.

Figure 5:
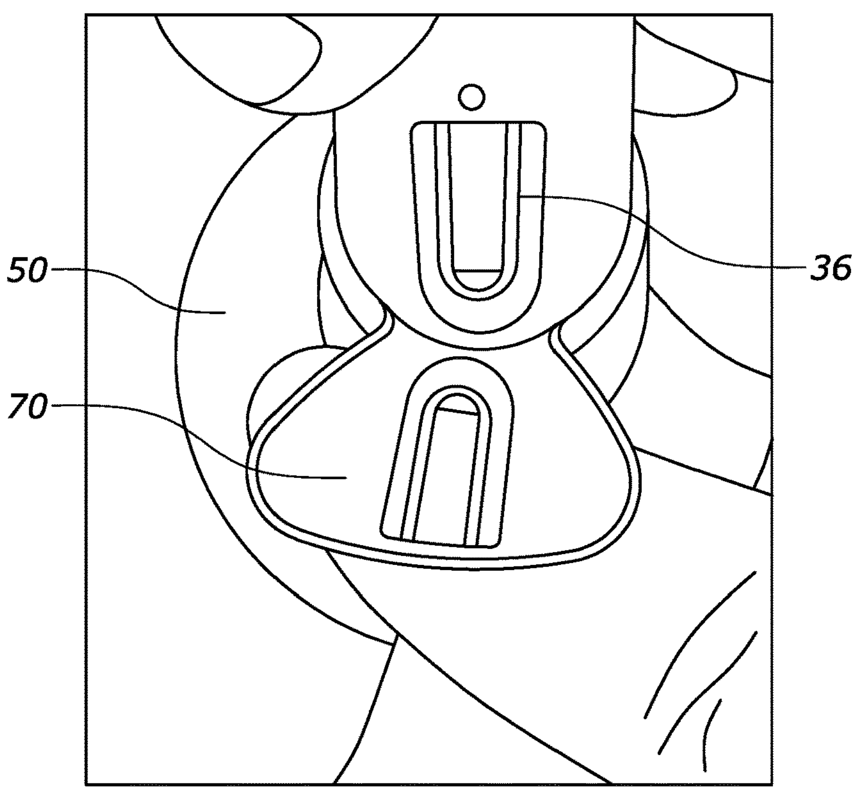
FIG. 5 is a perspective view of another exemplary drug delivery device assembly according to aspects of the present disclosure, where an injector window and the components within are visible in a reflective surface.
Figure 6:
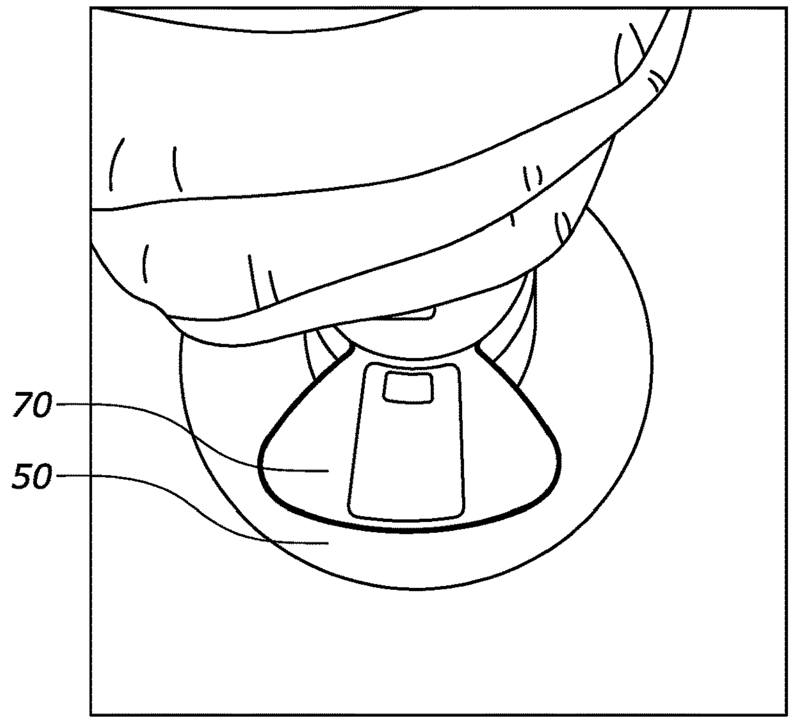
FIG. 6 is a perspective view of the exemplary drug delivery device assembly shown in FIG. 4, during a later stage in an injection sequence.

Another design consideration for position and angle of the flange is user preferred hand position. For example, during the injection sequence some users may choose to place their hand(s) near the viewing window, as shown in FIGS. 5 and 6. As shown in FIGS. 5 and 6, the orientation of the flange 54 permits a user to use this hand orientation while still observing the viewing window via the reflective surface 70.

Figure 3:
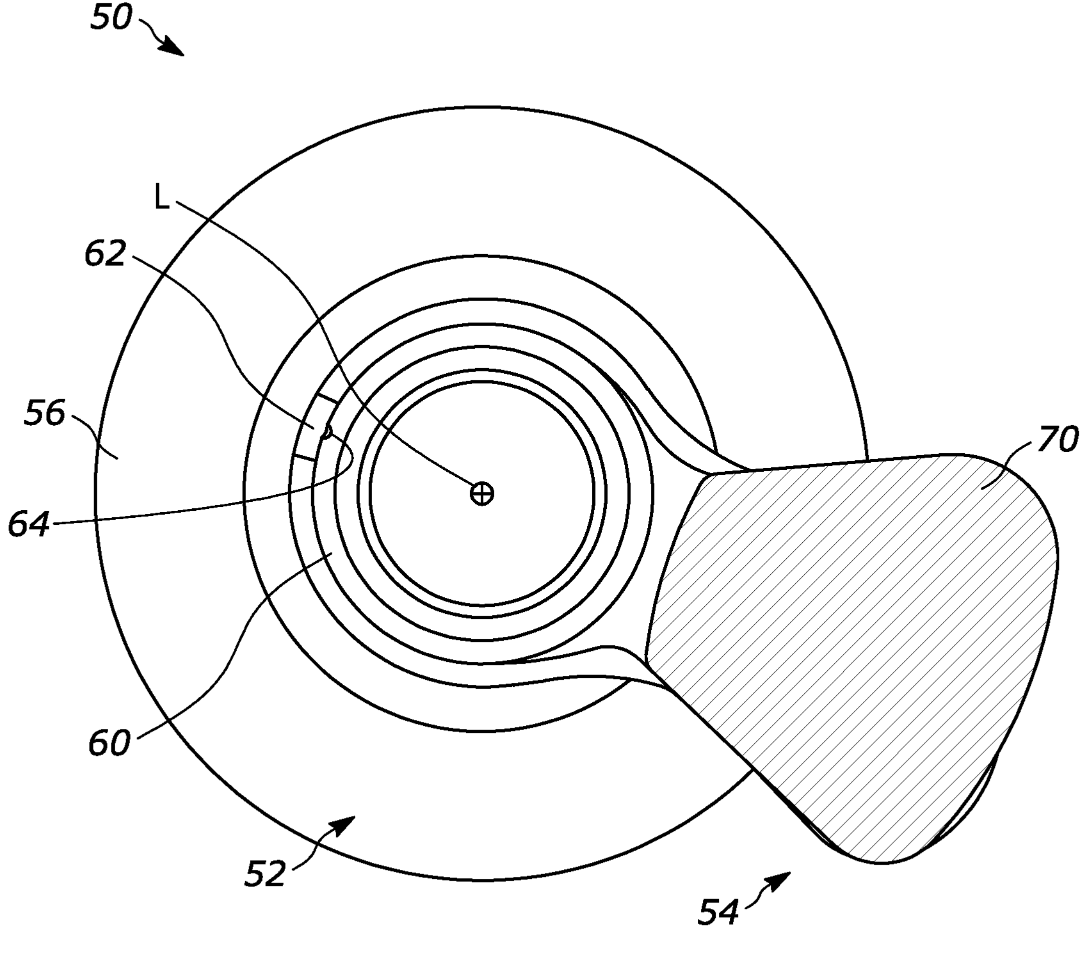
FIG. 3 is a top view of the exemplary accessory shown in FIG. 1.
Figure 4:
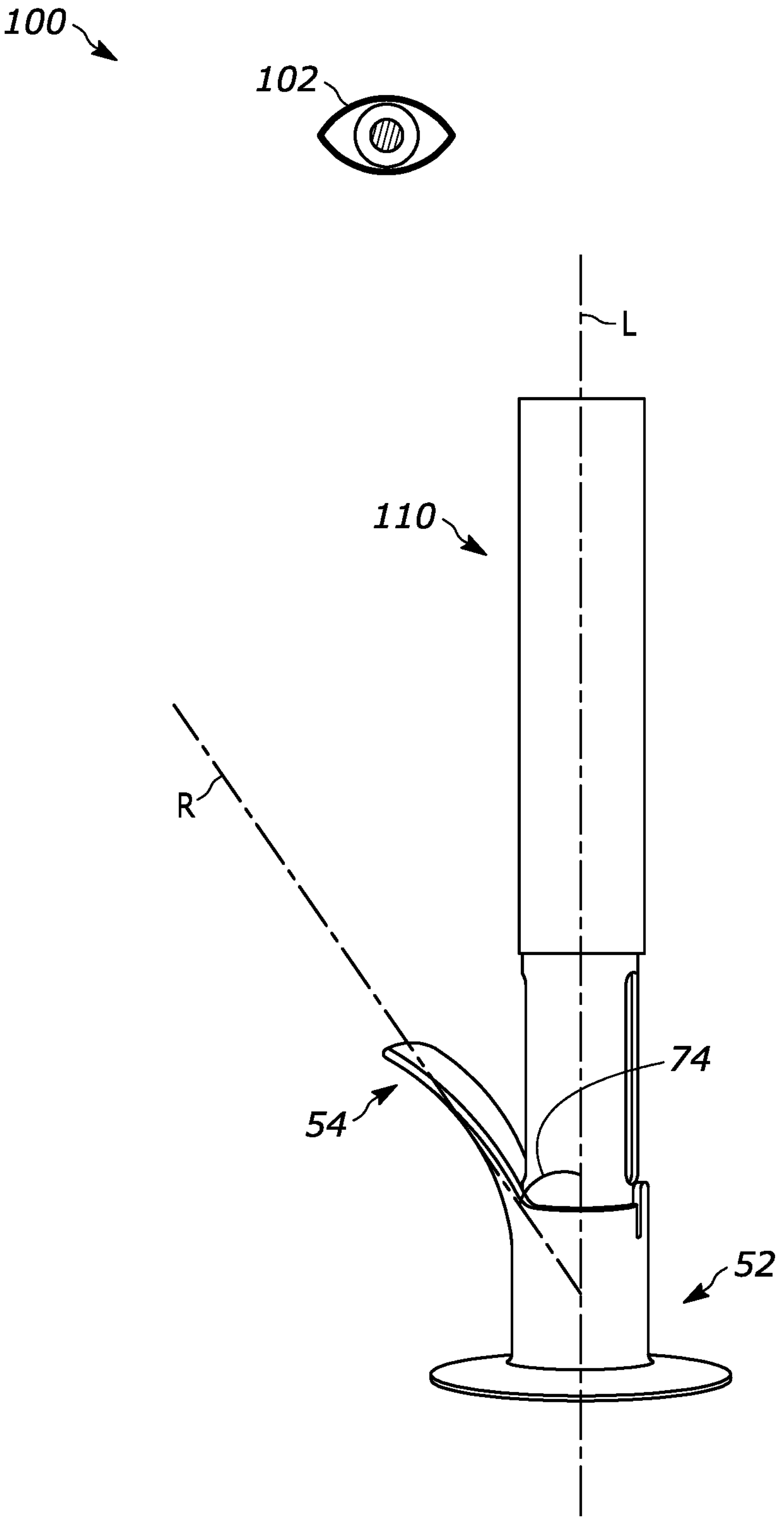
FIG. 4 is side view of an exemplary drug delivery device assembly according to aspects of the present disclosure, including an injector having a window and an accessory having a reflective surface positioned with respect to the injector such as to increase visibility of the injector window.

FIG. 4 shows a drug delivery device assembly 100, including an injector 110 and the accessory 50 from FIGS. 2 through 3. As discussed above, the angle 74 of the reflective surface 70 may be fixed or adjustable.

Figure 7:
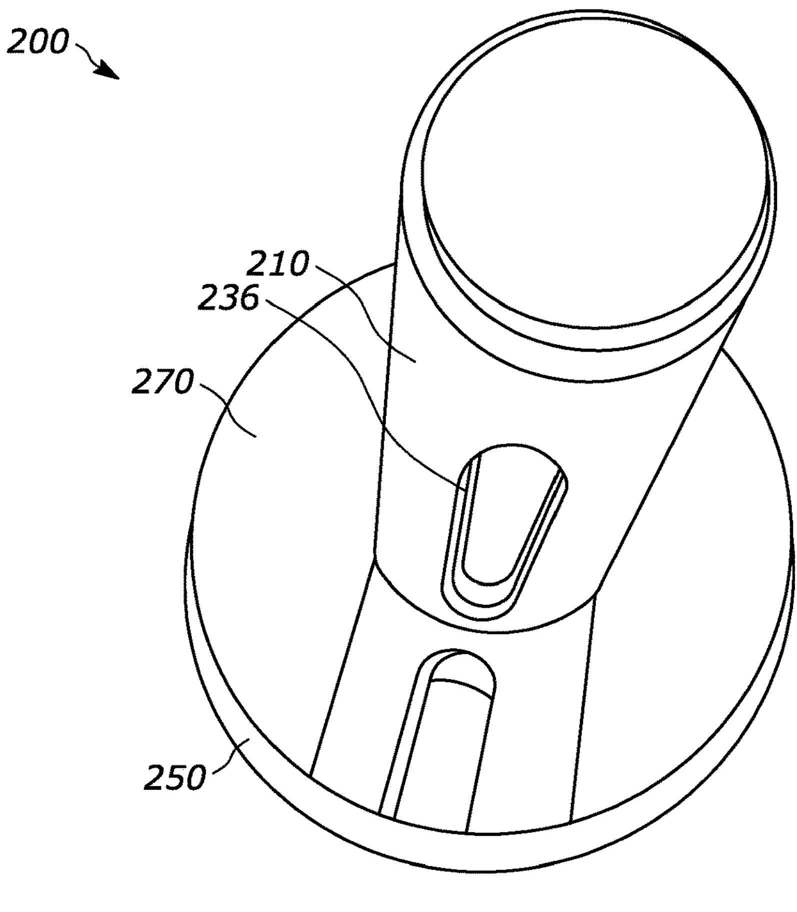
FIG. 7 is a perspective view of another exemplary drug delivery device assembly according to aspects of the present disclosure, where an injector window and the components within are visible in a reflective surface.
Figure 8:
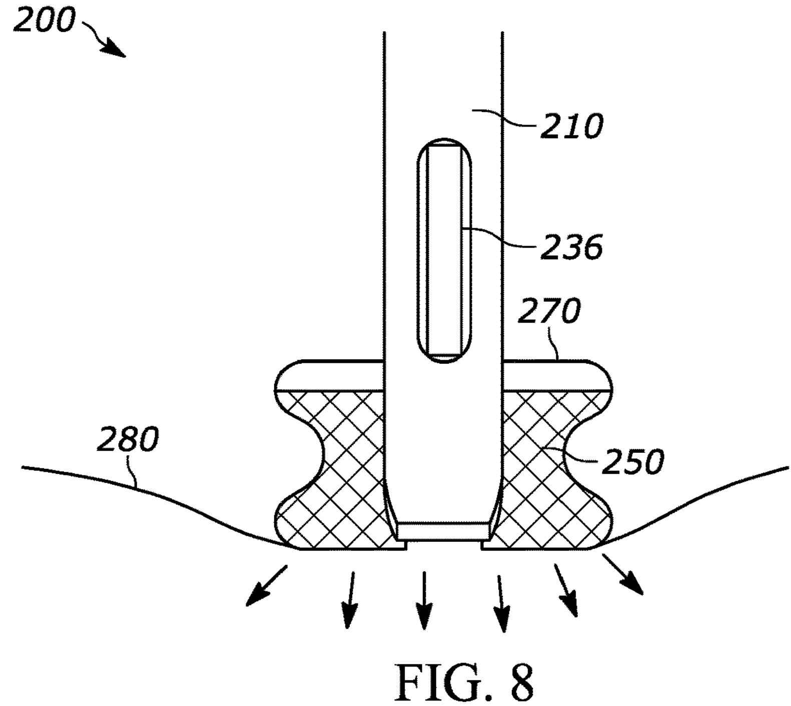
FIG. 8 is a side view of the drug delivery device assembly shown in FIG. 7.

FIGS. 7 and 8 show another exemplary drug delivery device assembly 200 according to aspects of the present disclosure, where a drug delivery device 210 having an injector window 236 is coupled with an accessory 250 having a reflective surface 270 configured to increase visibility of certain components or portions of the drug delivery device 210. For example, the window 236 is visible in the reflective surface 270, as shown in FIG. 7. The accessory 250 shown in FIGS. 7 and 8 includes a disc-shaped adapter 252 defining a cylindrical shaped inner surface 253 for receiving the drug delivery device 210 and a generally circular/donut shaped reflective surface 270 on the top (proximal) portion of the adapter 252. The adapter 254 and the drug delivery device 210 may have components for selectively coupling the same, such as a press-fit connection, a latching connection, or another suitable selective coupling arrangement. In addition to coupling the reflective surface 270 and the drug delivery device 210, the adapter 252 may also serve to provide a wider contact surface area with the injection site, as shown in FIG. 8. For example, because the adapter 252 has a larger diameter than the distal end of the drug delivery device 210, the contact forces acting on the users skin 280 may be more spread out, the user's skin 280 may be less likely to buckle or fold during contact, and/or it may be easier for the user to hold the drug delivery device 210 in the desired orientation. The reflective surface 270 shown in FIGS. 7 and 8 covers the entire upper surface of the accessory 250, thereby giving the user a 360 degree reflective view of the injector and potentially making it easier to improve the visibility of the window 236 from various angles.

The syringe barrel may have a length of 45 to 85 mm, 60 to 65 mm, or another suitable length. The length of the syringe barrel is the length between the rear end to the outlet to which the needle is attached (but not including the needle, if present).

The syringe barrel may have an internal diameter of 4 to 6.5 mm. If the syringe has a nominal maximum fill volume of 1 ml, the internal diameter of the syringe barrel may be 5.5 to 6.5 mm. If the syringe has a nominal maximum fill volume of 0.5 ml, the internal diameter of the syringe barrel may be 4 to 5 mm.

The wall of the syringe barrel may have a thickness of at least 1 mm; about 1 to 3 mm; about 1.5 to 3 mm; or about 2.4 to 2.8 mm. Due to the thickness of the wall, the sterilizing gas is restricted or prevented from entering interior of the syringe, thereby minimizing or preventing contact with the liquid formulation contained within the prefilled syringe.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the 0X40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); Ova-Rex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™ Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MY0-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) molecules such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF α monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)-N-((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl)ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a $KRAS^{G12C}$ small molecule inhibitor, or another product containing a $KRAS^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)× anti-CD3 BiTE® (bispecific T cell engager) construct. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1(PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device assembly comprising:

an injector housing having a body with a proximal end, a distal end, a longitudinal axis extending between the proximal end and the distal end, and a window;

a needle assembly at least partially disposed within the body, the needle assembly comprising a syringe barrel containing a medicament and a needle or a cannula, at least a portion of the syringe barrel positioned such as to be visible through the at least one window;

a drive assembly at least partially disposed within the body and operably coupled with the needle assembly to urge the medicament through the needle or cannula during an injection sequence; and an accessory, comprising:

a base portion;

a cylindrical shaped inner surface extending from the base portion along a longitudinal axis, the base portion configured to be operably coupled with the injector housing of the drug delivery device;

a reflective surface extending from the cylindrical shaped inner surface and positioned with respect to the window such as to increase visibility of the syringe barrel, wherein:

the reflective surface includes a reflector axis extending longitudinally within a plane of the reflective surface and intersecting the longitudinal axis at an angle between 15 and 75 degrees.

2. The drug delivery device assembly as in claim 1, further comprising a plunger stopper disposed within the syringe barrel and operably coupled with the drive assembly to urge the medicament through the needle or cannula during the injection sequence.

3. The drug delivery device assembly as in claim 2, wherein the reflective surface is positioned with respect to the window such as to increase visibility of the plunger stopper during the injection sequence.

4. The drug delivery device assembly as in claim 3, wherein the reflective surface is positioned with respect to the window such that during the injection sequence the plunger stopper is visible via the reflective surface from a position along the longitudinal axis and proximal of the proximal end of the injector housing.

5. The drug delivery device assembly as in claim 1, wherein the accessory includes a sleeve portion defining the cylindrical shaped inner surface and configured to receive at least a portion of the injector housing.

6. The drug delivery device assembly as in claim 1, wherein the base portion defines a distal portion of the accessory and wherein the sleeve portion extends from the base portion generally parallel to the longitudinal axis.

7. The drug delivery device assembly as in claim 1, wherein the angle of the reflective surface with respect to the longitudinal axis is adjustable.

8. The drug delivery device assembly as in claim 1, wherein the angle is (a) between 30 and 60 degrees, (b) between 40 and 50 degrees, or (c) approximately 45 degrees.

9. An accessory for a drug delivery device, comprising:

a base portion;

a cylindrical shaped inner surface extending from the base portion along a longitudinal axis, the base portion configured to be operably coupled with the drug delivery device, the drug delivery device having:

an injector housing having a body with a proximal end, a distal end, and at least one window, a needle assembly at least partially disposed within the body, the needle assembly comprising a syringe barrel containing a medicament and a needle or a cannula, at least a portion of the syringe barrel positioned such as to be visible through the at least one window, and a drive assembly at least partially disposed within the body and operably coupled with the needle assembly to urge the medicament through the needle or cannula during an injection sequence; and a reflective surface extending from the cylindrical shaped inner surface and positioned with respect to the window such as to increase visibility of the syringe barrel, wherein:

the reflective surface includes a reflector axis extending longitudinally within a plane of the reflective surface and intersecting the longitudinal axis at an angle between 15 and 75 degrees.

10. The accessory as in claim 9, further comprising a sleeve portion defining the cylindrical shaped inner surface and configured to receive at least a portion of the injector housing.

11. The accessory as in claim 10, wherein the base portion defines a distal portion of the accessory and wherein the sleeve portion extends from the base portion along the longitudinal axis.

12. The accessory as in claim 9, wherein the angle of the reflective surface with respect to the longitudinal axis is adjustable.

13. The drug delivery device assembly as in claim 12, wherein the angle between the reflective surface and the longitudinal axis is (a) between 30 and 60 degrees, (b) between 40 and 50 degrees, or (c) approximately 45 degrees.

14. The accessory as in claim 9, wherein the reflective surface includes a concave portion curved around the reflector axis, the concave portion configured to be generally aligned with the at least one window of the drug delivery device.

15. The accessory as in claim 9, wherein the reflective surface includes a mirror comprising glass or metal.

16. The accessory as in claim 9, wherein the plane of the reflective surface is flat or a contoured shape.

* * * * *